(12) United States Patent
Rutter et al.

(10) Patent No.: US 7,169,554 B2
(45) Date of Patent: Jan. 30, 2007

(54) MONITORING OLIGONUCLEOTIDE BINDING PROCESSES USING CHEMILUMINESCENCE QUENCHING

(75) Inventors: Andrew James Rutter, Cardiff (GB); Ian Weeks, Cardiff (GB); Zhaoqiang Li, Cardiff (GB); Keith Smith, Swansea (GB)

(73) Assignee: Gen-Probe Incorporated, San Diego, CA (US)

( * ) Notice: Subject to any disclaimer, the term of this patent is extended or adjusted under 35 U.S.C. 154(b) by 446 days.

(21) Appl. No.: 10/149,146

(22) PCT Filed: Dec. 11, 2000

(86) PCT No.: PCT/GB00/04721

§ 371 (c)(1),
(2), (4) Date: Aug. 12, 2002

(87) PCT Pub. No.: WO01/42497

PCT Pub. Date: Jun. 14, 2001

(65) Prior Publication Data

US 2003/0082713 A1    May 1, 2003

(30) Foreign Application Priority Data

Dec. 10, 1999    (GB) ................... 9929148.6

(51) Int. Cl.
C12Q 1/68 (2006.01)
C07H 21/02 (2006.01)
C07H 21/04 (2006.01)

(52) U.S. Cl. ............... 435/6; 536/23.1; 536/24.3
(58) Field of Classification Search ............ 435/6; 536/23.1, 24.3
See application file for complete search history.

(56) References Cited

U.S. PATENT DOCUMENTS

| | | |
|---|---|---|
| 4,277,437 A | 7/1981 | Maggio |
| 4,996,143 A | 2/1991 | Heller et al. |
| 5,658,737 A | 8/1997 | Nelson et al. |
| 5,691,145 A | 11/1997 | Pitner et al. |
| 5,691,146 A | 11/1997 | Mayrand |
| 5,840,873 A | 11/1998 | Nelson et al. |
| 5,866,336 A | 2/1999 | Nazarenko et al. |
| 5,888,739 A | 3/1999 | Pitner et al. |
| 5,925,517 A | 7/1999 | Tyagi et al. |
| 5,928,862 A | 7/1999 | Morrison |
| 5,935,517 A | 8/1999 | Roll et al. |
| 5,935,791 A | 8/1999 | Nadeau et al. |
| 6,090,552 A | 7/2000 | Nazarenko et al. |
| 6,117,635 A | 9/2000 | Nazarenko et al. |
| 6,130,047 A | 10/2000 | Nadeau et al. |
| 6,150,097 A | 11/2000 | Tyagi et al. |
| 6,783,948 B1 * | 8/2004 | Jiang et al. .......... 435/18 |

FOREIGN PATENT DOCUMENTS

| | | |
|---|---|---|
| EP | 0 070 685 | 1/1983 |
| EP | 0 070 685 A | 1/1983 |
| EP | 0 439 036 A | 7/1991 |
| EP | 0 439 036 A2 | 7/1991 |
| EP | 0 861 906 A1 | 9/1998 |
| WO | WO 95/13399 | 5/1995 |
| WO | WO 96/15270 | 5/1996 |
| WO | 97/01763 A | 1/1997 |
| WO | WO97/39008 A1 | 10/1997 |
| WO | 98/53316 A | 11/1998 |
| WO | WO 98/53316 | 11/1998 |
| WO | WO 99/11813 | 3/1999 |
| WO | WO 99/21881 | 5/1999 |
| WO | WO 99/22018 | 5/1999 |
| WO | 99/42615 A | 8/1999 |
| WO | WO 99/45142 | 9/1999 |
| WO | WO 99/49293 | 9/1999 |
| WO | WO 00/79009 A2 | 12/2000 |
| WO | WO 01/42497 A3 | 6/2001 |

OTHER PUBLICATIONS

Marras et al. Genetic Analysis : Biomolecular Engineering 14: 151-156 (Feb. 1999).*
Ashok Patel et al.; Clin. Chem. vol. 29, No. 9, pp. 1604-1608; 1983.

* cited by examiner

Primary Examiner—Ethan Whisenant

(57) ABSTRACT

Oligonucleotide building processes are monitored by means of an oligonucleotide probe which in one embodiment is labelled at one end with a chemiluminescent label and at the other end with a quencher molecule. The conformation of the oligonucleotide probe changes according to whether the probe hybridises with a substantially complementary nucleic acid sequence. In the non-hybridised state the chemiluminescent label is sufficiently close proximity to the quencher that the chemiluminescent emission is substantially attenuated, but in the hybridised state the separation is such that there is little or no attenuation. Particular probes and emitter/quencher pairs are disclosed.

26 Claims, 3 Drawing Sheets

Figure 3. Dose response of Hics probe to synthetic target oligonucleotide.

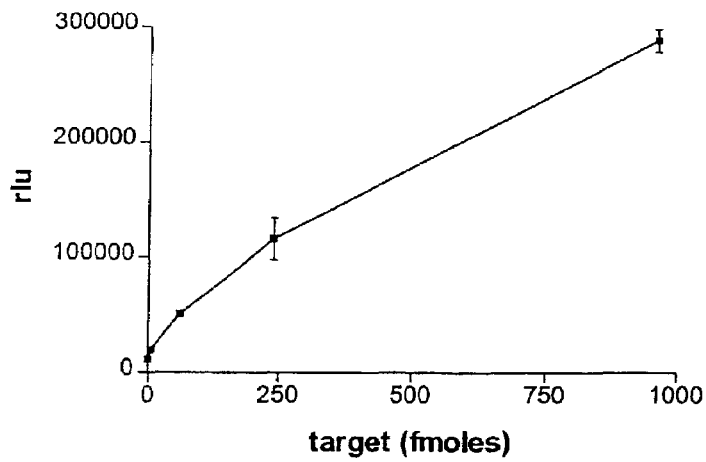

rlu – relative light units error bars are ± 1 standard deviation of duplicate determinations.

Figure 4. Measurement of T7 Polymerase product.

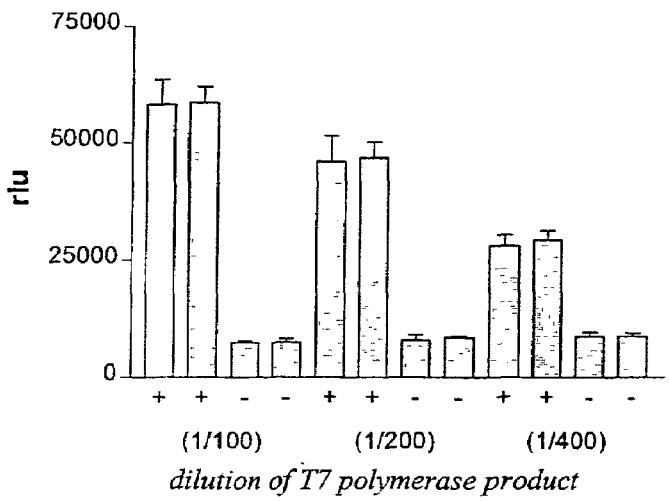

T7 polymerase in vitro transcription was performed in duplicate, and measurement of product using a HICS probe was performed in duplicate on each duplicate sample.

rlu – relative light units error bars are ± 1 standard deviation of duplicate determinations.

Figure 5. Analysis of mismatched base pairs
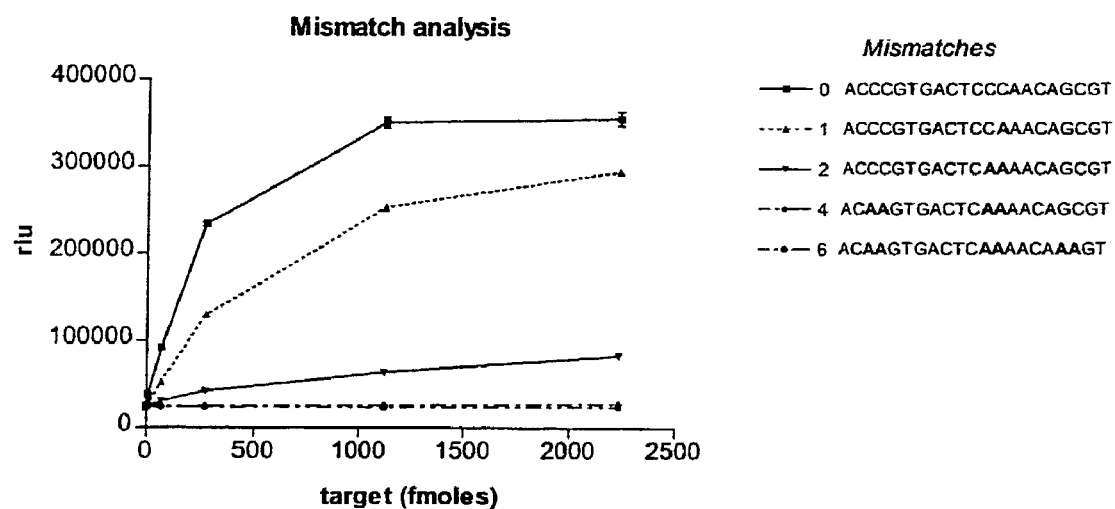
*rlu — relative light units*
*error bars are ± 1 standard deviation of duplicate measurements.*

SEQUENCE LISTING

<160> NUMBER OF SEQ ID NOS: 8

<210> SEQ ID NO 1
<211> LENGTH: 40
<212> TYPE: DNA
<213> ORGANISM: Artificial
<220> FEATURE:
<223> OTHER INFORMATION: Synthetic Oligonucleotide Probe

<400> SEQUENCE: 1
ccggtccagg tggagcaatg atcttgatct tcatgaccgg        40

<210> SEQ ID NO 2
<211> LENGTH: 36
<212> TYPE: DNA
<213> ORGANISM: Artificial
<220> FEATURE:
<223> OTHER INFORMATION: Synthetic Oligonucleotide Probe

<400> SEQUENCE: 2
ccggtcggcc tcttcgctat tacgccagct gaccgg                              36

<210> SEQ ID NO 3
<211> LENGTH: 33
<212> TYPE: DNA
<213> ORGANISM: Artificial
<220> FEATURE:
<223> OTHER INFORMATION: Synthetic Oligonucleotide Probe

<400> SEQUENCE: 3
ccggtcacgc tgttgggagt cacgggtgac cgg                                 33

<210> SEQ ID NO 4
<211> LENGTH: 21
<212> TYPE: DNA
<213> ORGANISM: Artificial
<220> FEATURE:
<223> OTHER INFORMATION: Synthetic Oligonucleotide Target

<400> SEQUENCE: 4
acccgtgact cccaacagcg t                                              21

<210> SEQ ID NO 5
<211> LENGTH: 21
<212> TYPE: DNA
<213> ORGANISM: Artificial
<220> FEATURE:
<223> OTHER INFORMATION: Synthetic Oligonucleotide Target

<400> SEQUENCE: 5
acccgtgact ccaaacagcg t                                              21

<210> SEQ ID NO 6
<211> LENGTH: 21
<212> TYPE: DNA
<213> ORGANISM: Artificial
<220> FEATURE:
<223> OTHER INFORMATION: Synthetic Oligonucleotide Target

<400> SEQUENCE: 6
acccgtgact caaaacagcg t                                              21

<210> SEQ ID NO 7
<211> LENGTH: 21
<212> TYPE: DNA
<213> ORGANISM: Artificial
<220> FEATURE:
<223> OTHER INFORMATION: Synthetic Oligonucleotide Target

<400> SEQUENCE: 7
acaagtgact caaaacagcg t                                              21

<210> SEQ ID NO 8
<211> LENGTH: 21
<212> TYPE: DNA
<213> ORGANISM: Artificial
<220> FEATURE:

-continued

```
<223> OTHER INFORMATION: Synthetic Oligonucleotide Target

<400> SEQUENCE: 8
acaagtgact caaaacaaag t                                              21
```

MONITORING OLIGONUCLEOTIDE BINDING PROCESSES USING CHEMILUMINESCENCE QUENCHING

This application is the national phase under 35 U.S.C. § 371 of PCT International Application No. PCT/GB00/04721 which has an International filing date of Dec. 11, 2000, which designated the United States of America.

FIELD OF THE INVENTION

This invention relates to monitoring the association and/or dissociation of ligand-binding pairs using chemiluminescence quenching. The invention provides for a chemiluminescent molecule (the emitter) and an energy absorbing molecule (the quencher) in which the chemiluminescence of the emitter is attenuated by the quencher when they are both incorporated as part of a molecular complex. More specifically, these molecules can be used as labels for nucleic acid hybridisation assays.

BACKGROUND OF THE INVENTION

The use of various types of label or reporter molecule for monitoring ligand binding reactions is well-established. Some of the earliest examples of these approaches involved the use of radioactive isotopes (radioimmunoassay, RIA) and enzymes (enzyme linked immunosorbent assay, ELISA). More recently, luminescent end-points such as those involving the use of fluorescent molecules and chemiluminescent molecules have been described. All these systems rely on the ability to incorporate the label into a ligand and to detect the binding of the labelled ligand to its binding partner. Generally, these procedures require the physical separation of bound and unbound labelled ligand in order to establish the presence or absence of the binding partner. However, many examples exist in which the binding of the labelled ligand to its binding partner results in a change in the chemical or physical properties of the label itself such that no prior separation of the binding complex is required. Examples of this include inhibition of enzyme activity upon binding of an enzyme-labelled ligand (KE Rubenstein et al (1972) *Biochem Biophys Res Comm*, 47, 846), change of fluorescence polarisation characteristics upon binding of a fluorescent labelled ligand (W B Dandliker et al (1973) *Immunochemistry* 10, 219) and, more recently, change in chemical reactivity of chemiluminescent labels upon nucleic acid duplex formation (U.S. Pat. No. 5,283,174).

These methods have formed the basis of numerous classes of binding assay such as immunoassay, nucleic acid hybridisation assay and receptor binding assay. The subsequent techniques have been applied to a wide range of applications including for example the detection of viruses in blood samples, the measurement of hormone levels, the detection of genetic mutations and the detection of contaminants in the environment.

DESCRIPTION OF THE PRIOR ART

Changes in optical properties of luminescent labels have been particularly exploited. In certain situations, it has been found that the binding partner itself can induce physicochemical changes in the labelled ligand. Such changes have been acknowledged to be variable in their nature and only observable in certain specific situations (M Pazzagli et al (1982) In: *Luminescent Assays: Perspectives in in Endocrinology and Clinical Chemistry*, M Serio and M Pazzagli (eds.), Raven Press, New York, p. 191) and are not therefore widely usable. In order to overcome these problems attempts have been made to introduce chemical entities of defined optical characteristics which are capable of modifying the optical properties of the labelled ligand in a defined and predictable manner upon binding to its binding partner.

Fluorescence quenching using pairs of donor and acceptor molecules has been widely described. Here, use is made of optical quenching by energy transfer in which donor fluorescence is not observed when a suitable optical quenching molecule is positioned close to it. A particularly good example of this approach has been described in which a fluorescent label (the donor) and a quenching molecule (the acceptor) are present on a sequence of nucleotides (the ligand) (U.S. Pat. No. 5,876,930). In its normal form the conformation of the ligand is such that, when measured in a fluorimeter, emission from the fluorescent label is attenuated by the quenching molecule. However, when the appropriate complementary nucleic acid sequence (the binding partner) is present, the conformation of the labelled ligand changes such that the donor and acceptor pair become spatially separated. This results in the quenching effect of the acceptor being lost and thus fluorescence emission being observed.

Central to this approach is the use of donor/acceptor pairs whose optical properties are known to be compatible. For example it is important that the fluorescence spectrum of the donor overlaps completely with the absorption spectrum of the acceptor for maximum quenching and minimal background. Further, efficient intra-molecular quenching only occurs if the donor/acceptor pair are sufficiently close together to permit resonance energy transfer to occur (generally about 10 nm or less). It is thus important that any change upon binding of the fluorescent ligand must result in spatial separation of the donor/acceptor pair to the extent that quenching is no longer possible.

Though procedures involving fluorescent labels have been shown to be useful in certain situations, it is accepted that limitations exist in terms of the sensitivity of detection of fluorescent labels. Two of the major reasons for this are high background due to the requirement for incident radiation to excite the fluorescent label and interference from non-specific fluorescent substances in the analytical sample.

In another approach, changes in the optical properties of chemiluminescent labels have been engineered using energy transfer. Theoretically this should provide for increased sensitivity over fluorescent labels since chemiluminescence can be detected more sensitively than fluorescence. Here, a chemiluminescent donor has been used together with a fluorescent acceptor. In an example of this system (A Patel and A K Campbell (1983), *Clinical Chemistry*, 29, 1604) an antigen has been labelled with a chemiluminescent molecule (a luminol analogue) and its corresponding antibody with a fluorescent molecule (a fluorescein analogue). In the absence of binding to antibody, the emission detected in a luminometer corresponds to a wavelength of approximately 460 nm characteristic of the chemiluminescent molecule. Upon immune complex formation between the antigen and antibody the donor/acceptor pair become sufficiently close for resonance energy transfer to occur and emission is seen at approximately 525 nm which is characteristic of the fluorescent acceptor.

This approach requires a sensitive luminometer capable of monitoring two wavelengths simultaneously which necessitates the use of complex instrumentation. Moreover, the selection of donor/acceptor pairs is more critical since attention must be paid to the emission characteristics of the acceptor. The various difficulties associated with this method severely limit its utility and as a result the technique has not resulted in the development of workable systems in the same way as fluorescence quenching methods which are themselves severely limited in application by poor sensitivities of detection.

It is apparent that a need exists for a simple means of optical coupling which is capable of demonstrating greater sensitivity than that achievable using fluorescence quenching. Measurement of chemiluminescence emission offers greater sensitivity of detection than the measurement of fluorescence emission but its use in conjunction with energy transfer has not demonstrated significant usefulness.

The use of chemiluminescence quenching in competitive protein binding methods has been described (U.S. Pat. No. 4,277,437 but this reference does not give any suggestion as to how such methods could be used to detect or quantify nucleic acid sequences. Moreover, whilst many macromolecular species are mentioned in the above reference, it is acknowledged therein that effective quenching only occurs over distances of less than 10 nm. Since large macromolecular structures exceed this dimension it would be necessary to specify the relative positions of emitter and quencher for labelling purposes to ensure that the required quenching distance is achieved. U.S. Pat. No. 5,925,517 describes the use of fluorescent donor/quenching pairs and briefly alludes to the use of a chemiluminescent donor, but does not indicate how to apply the teaching in practice to the use of chemiluminescent donors. The document makes no attempt to address the problem that whilst it is possible to make use of fluorescent quenching under constant chemical conditions, by definition, chemiluminescence involves a chemical reaction which requires a change in chemical conditions. Thus, for example, the quencher molecule DABCYL described for use in the fluorescent system of the above cited reference, although having an absorption spectrum apparently compatible with a given chemiluminescent molecule, will not function as a quencher in such a chemiluminescent system.

Furthermore it is generally recognised that the conditions for initiating a chemiluminescent reaction to provide reproducible emission of light need careful control and the U.S. Pat. No. 5,925,517 gives no guidance as to how this may be achieved and yet permit quenching to occur.

Given the large number of extra considerations that must be given to the use of chemiluminescent labels as opposed to fluorescent labels, one skilled in the art would not be able to extrapolate the enablement for fluorescent labels to chemiluminescent labels without substantial experimentation. This is particularly so in view of the fact that there is also no enablement in the scientific literature which would aid one skilled in the art to develop workable chemiluminescent quenching systems in the context of nucleic acid hybridisation assays.

SUMMARY OF THE INVENTION

Accordingly we have developed methods for monitoring complementary nucleic acid binding reactions which re on the use of chemiluminescent emitters and associated quenchers, and we disclose herein certain particularly effective compounds for use in these methods. We have also developed further assay techniques particularly suited for use with the novel compounds.

In the present context, nucleic acid binding or nucleic acid hybridisation reactions are taken to include the binding of discrete nucleotide sequences within the total nucleic acid nucleotide sequence. Sequences such as this or nucleotide sequences which do not necessarily form part of a larger nucleic acid sequence are also referred to herein as oligonucleotides or oligonucleotide sequences. Such oligonucleotide sequences may constitute an analyte or component thereof to be detected, quantified or otherwise assayed and are known as target sequences or, alternatively, target nucleic acids. Oligonucleotide sequences which are capable of binding to a given target sequence, to yield for example a duplex, are termed oligonucleotide probe sequences. Such probe sequences may exist as discrete oligonucleotide sequences or be part of a larger oligonucleotide sequence which also possesses sequences which do not bind to the target sequence. It is also well established in the art that oligonucleotide sequences may be modified by, for example, covalent or non-covalent means for attachment of other chemical moieties to facilitate detection and/or solid-phase attachment. The term is also intended to cover peptide nucleic acids (PNAs).

According to one aspect of this invention, there is provided a method for detecting and/or quantifying a target nucleic acid sequence in a sample comprising:

contacting said sample with an oligonucleotide sequence containing at least a probe sequence capable of binding to said target nucleic acid wherein the said oligonucleotide is labelled with each of at least one chemiluminescent molecule and at least one quencher molecule capable of attenuating chemiluminescence from said chemiluminescent molecule, the chemiluminescent and quencher molecules being arranged so that the interaction thereof changes according to whether the probe sequence is bound to said target nucleic acid, such that in one of the bound and unbound states said chemiluminescence is substantially attenuated, and in the other thereof there is reduced or no attenuation by said quencher molecule of the chemiluminescence; and changing the conditions so as to cause the chemiluminescent molecule to undergo a chemiluminescent reaction; and monitoring the chemiluminescence emission and comparing said emission with that corresponding to the absence of said target nucleic acid.

Further aspects and preferred features are set out in the accompanying claims.

The present invention involves the use of chemiluminescent (emitter) labels and energy acceptor (quencher) labels as means of monitoring complementary nucleic acid binding reactions. The emitter/quencher pairs are chosen such that chemiluminescence emission is attenuated when the emitter is in close proximity to the quencher. Typically, efficient quenching occurs when the distance between the emitter and the quencher is of the order of 10 nm or less. According to the preferred embodiments of the invention, the emitter and quencher labels can be coupled to oligonucleotide sequences which contain at least an oligonucleotide probe sequence such that the presence or absence of binding of complementary nucleic acids results in a change in the spatial separation of the emitter and quencher. This is manifest as a change in the intensity of chemiluminescence emission. Importantly, account is taken of the chemical conditions required to bring about a given chemiluminescent reaction and the quencher label optimised on this basis.

Preferably, the emitter and quencher molecules are covalently coupled to the oligonucleotides. Suitable means of attachment of small molecules, such as the emitters and quenchers of the present invention, to oligonucleotides are well established in the art and methods therefor are extensively published in the scientific literature.

The described examples provide a chemiluminescent system whose chemical conditions are compatible with maintaining the integrity of the nucleic acid duplexes and in which the intermolecular distance between the emitter and quencher is appropriate for the quenching process to occur at the instant of the chemiluminescent reaction.

Individually, it is known from the literature under what conditions chemiluminescent reactions can be brought about and under what conditions nucleic acid duplexes are stable. Further it is known that efficient energy transfer occurs over distances of approximately 10 nm or less. Taking into account the mutual chemical/physical compatibility of the chemiluminescent reaction and the nucleic acid duplex, we then identify a quencher molecule whose absorption characteristics are compatible with quenching of the chemiluminescence emission. Under normal circumstances, chemical and physical properties of dye molecules are referenced to "standard" conditions, but the conditions required to allow a chemiluminescent reaction to be initiated and to generate reproducible light emission are far from standard and so the standard data relating to "dye molecules" are of little practical use. Thus we have studied the characteristics of putative quencher molecules under the chemical/physical conditions required for chemiluminescent reactions to provide a basis for determining other suitable quencher molecules using the teachings disclosed herein.

In one aspect of the invention, a single stranded oligonucleotide sequence containing at least a probe sequence is constructed in such a way that its conformation allows for close proximity of emitter and quencher molecules when both are introduced into the sequence. Under such circumstances, chemiluminescence emission, when initiated in the appropriate manner, is attenuated. However, when the labelled oligonucleotide sequence is hybridised to a complementary target sequence, the induced conformational change causes the emitter/quencher pair to become spatially separated such that there is little or no attenuation and chemiluminescence is observable from the emitter. The observation of chemiluminescence is thus indicative of binding to the target sequence.

In another aspect, each of two different, respectively non-complementary, single stranded oligonucleotide sequences is labelled with an emitter and quencher respectively. Under such circumstances chemiluminescence, when initiated in the appropriate manner, is observed. The two labelled oligonucleotide sequences are hybridised to a target sequence which permits simultaneous hybridisation of both the labelled sequences to it such that both labelled sequences are bound in an adjacent or substantially adjacent manner such as to allow quenching to occur. In this situation, chemiluminescence is attenuated and indicates that simultaneous binding of the labelled sequences has occurred.

In yet another aspect, each of two complementary oligonucleotide sequences is respectively labelled with an emitter and a quencher. When the sequences react to form a duplex then quenching of the initiated chemiluminescence occurs. Presence of a nucleic acid sequence (such as a target sequence in an analytical sample for detection) complementary to either of these respective sequences results in loss of quenching manifested as increased chemiluminescence emission.

In a further aspect, the sequences respectively labelled with the said chemiluminescent emitters and quenchers are composed of peptide nucleic acids (PNAs) which are capable of binding to target nucleic acid sequences. The preparation and properties of such PNAs are described in the literature (U Soomets et al 1999) and one skilled in the art would appreciate the means of use of such molecules in the context of the teachings disclosed herein.

Further aspects will be apparent to the skilled person given the knowledge that close proximity of the emitter to the quencher attenuates chemiluminescence and that spatial separation results in the ability to observe chemiluminescence. The intermolecular distance over which resonance energy transfer, and hence chemiluminescence quenching, occurs is well established and the skilled person will be able to design emitter and quencher labelled oligonucleotide sequences in which the difference in light intensity corresponding to the change between bound and unbound states can be maximised, based on the teachings herein.

In addition to the detection and quantitation of nucleic acid targets, the teachings herein may also be used to discriminate between target sequences which may be substantially the same but may differ from each other by as little as one nucleotide.

There are many well known chemiluminescent systems such as luminol, acridinium salts, oxalate esters and dioxetanes, though the invention extends to any other suitable chemiluminescent molecules that exist.

The quencher molecules of the present invention are molecules that absorb energy from the emitter and then preferably dissipate this energy through non-radiative processes or through long wavelength fluorescence or phosphorescence which is not detected by the measuring instrumentation, and the terms "quenching", "attentuation" etc. should be interpreted accordingly.

In a further aspect it may be advantageous to perform the optical measurement at the interface of the liquid to be investigated for the presence of target, and a solid support. The solid support can be used to fulfil several purposes such as, e.g., permitting the ligand-binding complex to be conveniently removed from interfering substances prior to quantitation of chemiluminescence. The use generally of solid supports in ligand-binding techniques is well-known. Commonly used solid matrices comprise either chemically or physically treated macro-surfaces such as the walls of reaction vessels (for example, microtitre plate wells or test tubes), other polymeric supports or particulates such as derivatised cellulose, dextran, polystyrene (and other polymenric materials), controlled pore glass and paramagnetic particles. Means of covalent or non-covalent attachment of a wide variety of both small and large molecules to such solid supports are equally well established. As a further example, the solid support may provide a means of transducing the optical signal. For example the solid support may be incorporated into or comprise a light-sensitive device based on semiconductor or polymeric material.

Suitable ways of chemically linking small molecules, such as chemiluminescent and quencher molecules, to each other or to larger molecules such as peptides, polypeptides, proteins, oligonucleotides, nucleic acids, other biologically relevant molecules and solid-phase matrices will be well known to those skilled in the art.

DETAILED DESCRIPTION OF THE INVENTION

The present invention relates to the use of chemiluminescent emitter and quencher molecules in combination as a means of detecting and/or quantifying binding of complementary nucleic acid sequences. The light emission from luminescent molecules can be attenuated or "quenched" by the presence of molecules capable of absorbing the energy corresponding to the light emission. Such quenching can occur between molecules (intermolecular) or within molecules (intramolecular).

In a particular situation, quenching can occur by resonance energy transfer from the emitting species to an acceptor species which is incapable of emission (quencher). Efficient quenching of this type only occurs if certain criteria are met. Firstly, the emitter and quencher must be in close proximity to each other (typically 10 nm or less); secondly, the emission spectrum of the donor and the absorption spectrum of the quencher must be coincident; thirdly, the quencher must possess a large extinction coefficient.

Ligand binding reactions such as are exemplified by antigen/antibody, complementary nucleic acid sequence, receptor/hormone, enzyme/substrate binding all share the common feature that molecular complexes are formed.

In a preferred aspect of the invention, an oligonucleotide sequence is synthesised, using established techniques, which comprises at least a sequence of nucleotides complementary to the sequence of the target nucleic acid to be detected. Additionally, the sequences are so constructed so as to provide "linker arms" at the ends of the oligonucleotide sequence in such a way that chemiluminescent emitters and quenchers can be covalently attached to the linkers. The linkers may also be situated within the bounds of the oligonucleotide sequence provided that the intermolecular distance between the emitter and quencher is sufficiently short so as to permit quenching when the probe is not bound to its complementary target but is sufficiently long to obviate quenching when the probe is bound to its complementary target.

In the aforementioned assembly a chemiluminescent emitter and quencher are chosen such that in the absence of the target sequence the affinity between the chemiluminescent emitter and quencher causes them to exist in close proximity to each other. Thus in this assembly, chemiluminescence will be quenched due to the close proximity of the quencher molecule to the emitter. In the presence of the target sequence to be detected, the interaction of the chemiluminescent emitter and quencher is disrupted in favour of inter-molecular binding of the probe sequence with the target sequence to be detected. As a result of this conformational change, the emitter and quencher become spatially separated resulting in loss of the quenching effect and thus increased chemiluminescence emission. Affinity arising from several interactions or combinations thereof can be envisaged. In a preferred aspect, use is made of the electrostatic attraction between an electron-deficient emitter and an electron-rich donor. It is recognised that the affinity between the emitter and the quencher must be overcome by the binding affinity of the oligonucleotide probe sequence to the said target sequence. The relative affinity of the emitter/quencher pair can be optimised by structural modification of the labels themselves or of the linkers. Further, affinity can be introduced by the introduction of other chemical species into the following regions of the oligonucleotide sequence; probe sequence, sequences situated adjacent to the probe sequence (ie flanking sequences), linkers, emitters, quenchers.

In another aspect, in the absence of the target sequence to be detected, the emitter and quencher are held in close proximity by a second, oligonucleotide sequence or "staple" which is complementary to groups of sequential nucleotides situated at the two ends of the probe sequence when the latter are positioned adjacent or substantially adjacent to each other. Preferably, the second oligonucleotide consists of a range of between four and sixteen nucleotides. The nucleotides bound by the second oligonucleotide or "staple" need not be a contiguous complement provided that the required duplex stability or melting temperature (Tm) is achieved and provided that the necessary intermolecular distances are achieved between emitter and quencher. The second oligonucleotide sequence may be complementary to elements of the probe sequence itself or to flanking regions introduced during synthesis which are not complementary to the target. Such flanking sequences preferably possess between two and eight nucleotides. Alternatively, instead of using a second oligonucleotide molecule to bridge the end of the first oligonucleotide sequence in the absence the target, this function may be achieved by the use of other forms of bridging molecule which bind stably to the first oligonucleotide to keep the emitter and the quencher in proximity in the absence of the target but which yield to allow the oligonucleotide preferably to bind to the target in the presence thereof.

In a further aspect of the invention, an oligonucleotide sequence is synthesised, using established techniques, which comprises a probe sequence of nucleotides complementary to the sequence of the target nucleic acid to be detected, together with flanking sequences which permit intra-molecular complementary binding to occur. Additionally, the sequences are so constructed so as to provide "linker arms" at the ends of or within the flanking sequences in such a way that chemiluminescent emitter and quencher molecules can be covalently attached to the linkers. Thus in this assembly, chemiluminescence will be quenched due to the close proximity of the quencher molecule to the emitter as a result of the intra-molecular complementary binding of the flanking regions. In the presence of the target sequence to be detected, the intra-molecular complementary binding of the flanking sequences is dissociated in favour of inter-molecular binding of the probe sequence with the target sequence to be detected. As a result of this conformational change, the emitter and quencher become spatially separated resulting in loss of the quenching effect and thus increased chemiluminescence emission. The emitter/quencher pair may also be incorporated into the probe sequence itself, as opposed to being present on the flanking sequences, provided that the quenching process. still occurs when no target nucleic acid is present and does not occur when target nucleic acid is present.

In the various possible aspects of the invention it may be advantageous to use a plurality of labels and quenchers. In one aspect it can be envisioned that the use of more than one molecule of the same emitter present in the same oligonucleotide sequence will result in greater light emission whereas the use of more than one quencher molecule will result in more extensive quenching. In a second aspect it can be envisioned that the use of a plurality of distinct emitters and quenchers will enable multiple analyses to be performed. Means of using a plurality of labels for the purpose of multiple analysis are well established for conventional ligand binding assays.

In one arrangement for monitoring two analytes two different mutually distinguishable oligonucleotide systems are used. In one example a first oligonucleotide probe has a chemiluminescent label at one end and a quencher at the other, and a second oligonucleotide probe has a distinguishable chemiluminescent label at one end and the same or a different quencher at the other.

Alternatively a first oligonucleotide system comprises a first oligonucleotide having a first sequence hybridising to a first target nucleic acid and labelled with a first chemiluminescence label, and a second oligonucleotide system comprises a second oligonucleotide having a second sequence hybridising to a second target nucleic acid, and labelled with a second chemiluminsence label. The first and second oligonucleotide systems also each include a further oligonucleotide which may be the same or different for each system, which hybridises to the respective target nucleic acids close to the first and second nucleotide probes, the further nucleotide or nucleotides having the same or different quenching molecules, such that binding of said further nucleotide to one of said target nucleic acid sequences causes quenching.

In all aspects of the invention the chemiluminescence intensity resulting from the presence of target nucleic acid in the sample to be tested is compared with the corresponding signal obtained or anticipated from a situation where the target is absent. The emission intensity is preferably, though not exclusively, detected and/or quantified using a luminometer. Methods for the detection and/or quantitation of chemiluminescence emission are well-known to those skilled in the art.

Methods of synthesising oligonucleotides of the desired sequence are well-established as are methods for the introduction of linkers, for attachment of emitters and quenchers, into the 3' or 5' ends of the sequence or within the body of the sequence. The probe sequence is selected so as to provide optimal complementary binding characteristics to the target sequence to be detected, selection of appropriate sequences being well-established in this field of the art. Preferably the probe sequence consists of between 15 and 45 nucleotides. The linkers for attachment of the emitter and quencher molecules are commercially available and widely used. A wide variety of such linkers are available which can be used in the present invention. Preferably the linkers are between 4 and 20 atoms in length and preferably possess amine or thiol functional groups or derivatives thereof. The methods involved in the synthesis of oligonucleotides containing such linker groups are established to the extent that it is possible to purchase the desired assembly to order from commercial suppliers. In a preferred aspect an assembly is synthesised which possesses a 3'-C7 primary amine terminated linker and a 5'-methoxytrityl protected thiol linker. The heterobifunctional nature of this assembly allows sequential linking of the emitter/quencher pair. In a preferred aspect, the assembly is first labelled with a chemiluminescent emitter containing an N-succinimidyl ester moiety to permit attachment to the amine linker. The product is purified following which the thiol linker is deprotected and the resulting modified assembly reacted with an iodoacetamide derivative of the quencher molecule. The emitter/quencher labelled assembly is then finally purified prior to use.

Numerous examples of molecules that exhibit chemiluminescence and numerous examples of molecules that absorb light are disclosed in the literature.

Thus in the preferred method, the chemiluminescent emission spectrum of the emitter is determined using established spectrometric methods. A quencher molecule is then selected which possesses the desired absorption characteristics under the same chemical conditions as are required to bring about chemiluminescence of the emitter. An important consideration is the observation of any change in absorption characteristics of the quencher with time. Thus, though the absorption characteristics may appear to be desirable immediately following exposure of the quencher to the relevant chemical environment, there may be a change to undesirable characteristics over the period of time required for the measurement of the emission from the chemiluminescent reaction to be completed. Alternatively, a putative quencher molecule which may not have favourable characteristics as determined in a generic solvent and published accordingly, may possess the desired characteristics in the chemical environment required for initiation of chemiluminescence from the emitter. As before, it is important to determine that these favourable characteristics are attained well within the time-scale required for the measurement of the chemiluminescence emission.

It is expected that many chemiluminescent molecules will have utility in the present invention but the chemiluminescent emitters are preferably molecules based on acridine or phenanthridine. More preferably the emitters are based on acridinium salts or acridans.

Similarly, many dyes could have utility as quenchers in the present invention with the proviso that their absorption spectra are known or can be determined under the chemical conditions required to facilitate chemiluminescence from the chosen emitter. Preferably, the quencher molecules are azo dyes with high molar extinction coefficients over the desired absorption wavelength range. The range of wavelengths of emission and absorption is preferably 200–700 nm. Means of chemically coupling small molecules, such as are exemplified by the emitters or quenchers alluded to herein, to large molecules such as oligonucleotides and other small molecules such as nucleotides are well established.

By careful consideration of the absorption characteristics of a range of putative quencher molecules at and immediately after initiation of the chemiluminescent reaction we have designed novel chemiluminescent assays for nucleic acids.

Whilst the invention has been described above, it extends to any inventive combination of features set out in this Specification.

The following examples are for the purpose of illustrating typical embodiments of the present invention and do not represent any limitations in the scope of the teachings herein.

Reference will be made to the accompanying drawings in which:—

FIG. 3 is a dose/response curve obtained using a HICS probe to measure the presence of a synthetic target oligonucleotide, plotting light output in relative light units (rlu) against the amount of target materials;

FIG. 4 is a graph showing measurement in duplicate of a T7 polymerase product using a HICS probe, at various dilutions of the polymerase product, and FIG. 5 is a graph showing the dose-response curves obtained for the reaction of HICS probe with a 100% complementary sequence and with increasingly mismatched sequences relative to the middle 21 bases of the HICS probe.

EXAMPLES

Figure 1:
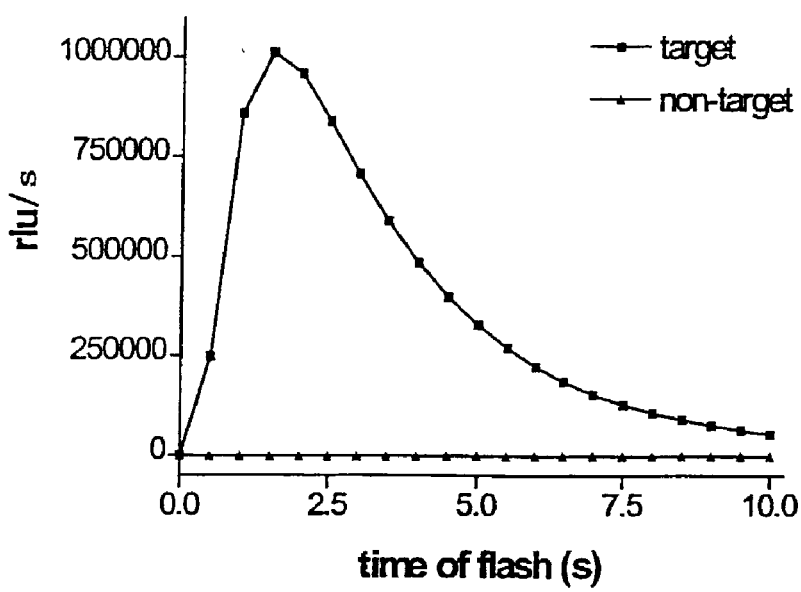
FIG. 1 is a graph illustrating the intensity/time curves for a chemiluminescence/quencher-labelled oligonucleotide probe (Hybridisation Induced Chemiluminescent Signal, (HICS), probe) according to the invention, when bound to its complementary target sequence and when not so bound.

1. Source of the Oligonucleotide.

The following oligonucleotide was synthesised using established methods by a commercial supplier. The sequence was as follows, CCGGTCCAGGTGGAGCAATGATCT-
TGATCTTCATGACCGG (SEQ ID No 1). The oligonucleotide was supplied with linkers at both ends, with a free amine group at the end of one linker and a trityl protected thiol group at the end of the other.

2. Synthesis of Dibromo-acridinium Ester (AE-NHS).

3-(3,5-Dibromo-4-hydroxyphenyl)propanoic acid

To a stirred solution of 3-(4-hydroxyphenyl)propanoic acid (1.011 g, 6.020 mmol) in glacial acetic acid (50 ml) at ambient temperature was added $Br_2$ (0.620 ml, 1.901 g, 12.03 mmol). The mixture was stirred in the dark for 70 h, after which evaporation of the solution in vacuo left a residue of 2.401 g. The residue was dissolved in diethyl ether (70 ml), and the solution was washed with saturated NaCl aq. (40 ml×3), dried ($Na_2SO_4$) and evaporated to leave a white powder (1.902 g). The product was recrystallised from benzene/hexane to give white needles of the desired product (1.760 g, 90%), mp 108–9° C. CI-MS m/z 324 [$M^+$, 100%], 278 [9], 265 [98], 244 [15], 198 [12], 185 [40].

Benzyl 3-(3,5-dibromo-4-hydroxyphenyl)propanoate

A solution of anhydrous benzyl alcohol (3.20 ml, 3.344 g, 0.309 mol), 3-(3,5-dibromo-4-hydroxyphenyl)propanoic acid (1.001 g, 3.090 mmol) and trifluoroacetic anhydride (2.50 ml, 3.703 g, 17.30 mmol), was heated at 85° C. for 3 h, then cooled and poured into aqueous sodium hydrogen carbonate (100 ml, 8% aq.). The mixture was exhaustively extracted with chloroform (70 ml×3) and the solvent was evaporated to leave a syrup (2.002 g). This residue was subjected to chromatography using a chromatotron [ethyl acetate:hexane (1:8; 1:4; 1:2 sequentially)] to give the desired product as a pure colourless oil (1.022 g, 80%) after evaporation of the solvent from the appropriate combined fractions. CI-MS m/z 432 [$(M+NH_4)^+$, 95%], 91 [100].

Acridine-9-carbonyl chloride

Acridine-9-carboxylic acid (1.730 g, 10 mmol) was dissolved in thionyl chloride (25 ml) and the solution was refluxed for 6 hours. The solution was concentrated in vacuo and hexane was added slowly to precipitate the product. The mixture was filtered to give a yellow solid (1.721 g, 94%), mp 218–9° C.

2,6-Dibromo-4-(2-benzyloxycarbonylethyl)phenyl acridine-9-carboxylate

Acridine-9-carbonyl chloride (170 mg, 0.70 mmol) was dissolved in anhydrous pyridine (10 ml). Benzyl 3-(3,5-dibromo-4-hydroxyphenyl)propanoate (250 mg, 0.70 mmol) was added and the mixture was stirred at room temperature for 18 h, then poured into ice-water (100 ml). The mixture was exhaustively extracted with $CHCl_3$ (50 ml×4) and the combined extracts were washed with saturated aq. NaCl (50 ml×2), dried ($Na_2SO_4$) and evaporated to give a yellow oil (340 mg). This residue was subjected to chromatography using a chromatotron (hexane:ethyl acetate, 4:1) and evaporation of the solvent from the combined fractions containing the product gave the desired product as a light yellow crystalline solid (231 mg, 75%), mp 114–5° C. FAB-MS m/z 619 [$M^+$, 45%], 206 [100], 179 [94].

2,6-Dibromo-4-(2-carboxyethyl)phenyl acridine-9-carboxylate

A mixture of 2,6-dibromo-4-(2-benzyloxycarbonylethyl)-phenyl acridine-9-carboxylate (191 mg, 0.309 mmol), glacial acetic acid (20 ml) and 48% hydrobromic acid (5 ml) was heated at 100° C. for 3 h and then cooled. The mixture was added to water (100 ml) and extracted with 20% methanol in chloroform (100 ml×4). The organic extracts were combined and evaporated and the residue was suspended in chloroform (50 ml) and neutralised with a slight excess of triethylamine. The mixture was washed with water (70 ml×3), and the organic layer was dried over sodium sulphate and evaporated to dryness. The residue was recrystallised from $CHCl_3$ to give the desired product (115 mg, 74%.), mp 240–2° C. FAB-MS m/z 529 [$M^+$, 75%], 511 [10], 486 [10], 207 [100].

2,6-Dibromo-4-(2-succinimidyloxycarbonylethyl) phenyl acridine-9-carboxylate N-Hydroxysuccinimide (12 mg, 0.10 mmol) and 2,6-dibromo-4-(2-carboxyethyl)phenyl acridine-9-carboxylate (50 mg, 0.090 mmol) were dissolved in anhydrous DMF (3 ml) and cooled to −20° C. Dicyclohexylcarbodiimide (DCC, 22 mg, 0.11 mmol) was added and the mixture was stirred at −20° C. for 2 h. The solution was stirred overnight at room temperature, and then evaporated to dryness. The residue was extracted with dichloromethane (50 ml) and the filtrate was evaporated to obtain the crude product (100 mg). Further purification was carried out by chromatotron, eluted with chloroform. The solvent was evaporated from the appropriate combined fractions to give the desired product as a light-brown solid (40 mg, 64%), mp 175–6° C. FAB-MS m/z 627 [$(M+1)^+$, 20%], 225 [100], 206 [18], 179 [10], 143 [8].

2,6-Dibromo-4-(2-succinimidyloxycarbonylethyl) phenyl 10-methylacridinium-9-carboxylate trifluoromethanesulfonate To a solution of 2,6-dibromo-4-(2-succinimidyl-oxycarbonylethyl)phenyl acridine-9-carboxylate (100 mg, 0.160 mmol) in dichloromethane (10 ml) under argon was added methyl trifluoromethanesulfonate (0.13 ml, 0.183 g, 1.12 mmol). The resulting solution was stirred overnight and the precipitate was filtered off and washed with anhydrous benzene to yield a yellow powder. Extensive washing with $CHCl_3$ gave the desired product as a yellow solid (113 mg, 90%), mp 320° C. FAB-MS m/z 641 [$(M-SO_3CF_3)^+$, 12%], 627 [85], 225 [34], 207 [6], 195 [100], 179 [32].

Synthesis of 2-(4-dimethylaminophenylazo)-N-[2-(2-iodoacetylamino)ethyl]benzamide (IA-methyl Red) Succinimidyl 2-[4-(dimethylamino)phenylazo] benzoate Methyl red (1.251 g, 4.65 mmol) in THF (30 ml) was cooled to 0° C. and dicyclohexylcarbodiimide (1.103 g, 5.3 mmol) was added, followed by N-hydroxysccinimide (0.568 g, 4.94 mmol). The mixture was stirred at 0° C. for 2 h, then the temperature was increased to room temperature and the mixture was stirred overnight. The white solid formed was removed by filtration, and the filtrate was evaporated to dryness to give a red solid. The solid was recrystallised from acetone-diethyl ether and then dried under vacuum to give a red solid (0.849 g, 50%), mp 124–126° C. FAB-MS m/z 361 [$(M+H)^+$, 23%], 252 [17], 132 [100].

N-[2-(t-Butoxycarbonylamino)ethyl]-2-[4-(dimethylamino)phenylazo]benzamide

To the activated ester obtained above (74 mg, 0.20 mmol) in dioxane (2 ml) was added t-butyl N-(2-aminoethyl) carbamate (99 mg, 0.63 mmol) in methanol (1 ml). The mixture was shaken at room temperature in the dark for 4 h. TLC (toluene:EtOAc 1:1) showed that all the starting material (Rf 0.85, violet) was converted into a new component (Rf 0.60, orange). Purification was carried out on a silica gel column eluted with toluene:EtOAc 1:1. An orange solid (75 mg, 91%) was obtained, mp 131–134° C. FAB-MS m/z 434 [(M+Na)$^+$, 6%), 412 [(M+H)$^+$, 50], 252 [82], 132 [100].

N-(2-Aminoethyl)-2-[4-(dimethylamino)phenylazo]benzamide

To the protected amine obtained above (70 mg, 0.17 mmol) in dioxane (2 ml) was added concentrated hydrochloric acid (0.6 ml). The orange solution turned to violet. The mixture was stirred at room temperature for 15 min and then evaporated to dryness. The residue was washed with dioxane (2×3 ml) and diethyl ether (3 ml) and was then dissolved in MeOH (4 ml). NaHCO$_3$ (saturated, 2 ml) was added and the mixture turned back to orange. Dichloromethane (20 ml) and then water (20 ml) were added. The organic layer was collected, dried over MgSO$_4$ and evaporated to give a red solid (42 mg, 79%), mp 119–124° C. FAB-MS m/z 312 [(M+H)$^+$, 13%), 252 [31], 132 [100].

2-(4-Dimethylaminophenylazo)-N-[2-(2-iodoacetylamino)ethyl]benzamide

To the amine obtained above (60 mg, 0.19 mmol) in dichloromethane (DCM, 5 ml) was added triethylamine (20 mg, 0.20 mmol). The mixture was cooled to 0° C. and iodoacetyl chloride (40 mg, 0.20 mmol) was added. After 5 min (at 0° C.), TLC (CH$_3$Cl:MeOH, 4:1) showed that most of the starting material (Rf 0.4) was converted into a new component (Rf 0.6). Stirring at 0° C. was maintained for another 5 min and the resulting mixture was then evaporated to dryness. The residue was re-dissolved in DCM (3 ml) and loaded onto a silica gel column, which was then eluted by CH$_3$Cl:MeOH, 7:1. Pure desired product (25 mg, 27%) was obtained by evaporating the solvent from the appropriate fractions, mp 140–142° C. FAB-MS m/z 480 [(M+H)$^+$, 75%), 252 [52], 107 [100].

3. Preparation of Chemiluminescence/Quencher-Labelled Oligonucleotide Probe (Hybridisation Induced Chemiluminescent Signal, Probe)—HICS (i) Coupling of AE-NHS The AE-NHS was coupled to the oligonucleotide via a free amine group at the end of a linker. The oligonucleotide to be labelled was evaporated to dryness in a microcentrifuge tube. After drying, a buffer solution (a mixture of N-(2-hydroxyethyl)piperazine-N'-(2-ethanesulfonic acid) (HEPES) buffer (0.125 M, pH 8.0) and dimethyl sulfoxide (DMSO); 1:1, v/v) (8 µl) was added, followed by AE-NHS in DMSO (2 µl, 25 mM). The contents were gently mixed and then incubated for 20 min at 37° C. Additional AE-NHS in DMSO (3 µl, 25 mM) was added, and the contents were mixed and incubated for a further 20 min at 37° C. The labelling reaction was quenched by addition of lysine dissolved in the same buffer solution (5 µl, 0.125 M). The contents were mixed gently and incubated for 5 min at room temperature. Sodium acetate (30 µl, 3 M, pH 5.0), water (245 µl) and glycogen (5 µl, 40 mg/ml) were added to the tube and the contents were gently mixed. Chilled (−20° C.) absolute ethanol (640 µl) was added and the contents were mixed by vortexing. The tube was incubated on dry ice for 10 min and then centrifuged at 15,000 rpm in a refrigerated (4° C.) centrifuge. The supernatant was carefully aspirated and the pellet was re-suspended in sodium acetate buffer (20 µl, 0.1 M, pH 5.0) containing lithium lauryl sulfate (0.1%, w/v).

(ii) Purification of Labelled Oligonucleotide

The labelled oligonucleotide was purified by hplc on a C-4 reverse phase column, utilising a linear elution gradient of 25–70% of buffer B in buffer A. Buffer A is aqueous triethylammonium acetate buffer (0.1 M, pH 7.0) and B is triethylammonium acetate buffer in 75% acetonitrile (0.1 M, pH 7.0). The flow rate was 1 ml/min, and 0.5 ml fractions were collected for 25 min. The absorption was monitored at 260 nm. Immediately after collection, aqueous lithium lauryl sulfate (10 µl, 10%, w/v) was added to each of the fractions and after vortexing the contents were transferred to a microcentrifuge tube. The chemiluminescence of each fraction was measured as follows. An aliquot (0.5 µl) of each fraction was pipetted into a separate 12×75 mm polystyrene tube containing aqueous lithium lauryl sulfate (100 µl, 0.1%) and was then vortexed. The chemiluminescence was measured using a luminometer. This involved the automatic injection of hydrogen peroxide solution (200 µl, 1.0%, v/v in 2-amino-2-(hydroxymethyl)propane-1,3-diol hydrochloride (Tris-HCl) buffer solution (0.2 M, pH 9.0)), followed by measurement of signal for 10 seconds. The chemiluminescence was plotted as relative light units (rlu) against fraction number.

(iii) Recovery of AE-NHS Labelled Oligonucleotide

The AE-NHS labelled oligonucleotide was precipitated and recovered as follows. To each of the desired fractions, sodium acetate buffer (30 µl, 3 M, pH 5.0), water (245 µl) and glycogen (5 µl, 40 mg/ml) were added and the contents were gently mixed. Chilled (−20° C.) absolute ethanol (640 µl) was added and the contents were mixed by vortexing. The tube was incubated on dry ice for 10 min and then centrifuged at 15,000 rpm in a refrigerated (4° C.) centrifuge. The supernatant was carefully aspirated and the pellet was re-suspended in sodium acetate buffer (20 µl, 0.1 M, pH 5.0) containing lithium lauryl sulfate (0.1%, w/v).

(iv) Coupling of Methyl Red

To the product of (iii) was added triethylammonium acetate buffer (200 µl, 0.1 M, pH 7.0). The protective trityl group was removed from the thiol by the addition of aqueous silver nitrate (6.7 µl, 0.01 M) and the mixture was incubated for 30 minutes at room temperature. Aqueous dithiothreitol (10 µl, 0.01 M) was added and the mixture was incubated for 5 minutes at room temperature with shaking. The mixture was centrifuged at 10,000 rpm for 2 minutes and the supernatant was carefully removed from the pellet and transferred to a fresh microcentrifuge tube, then NaHCO$_3$ buffer (195 µl, 0.1 M, pH 9.0) was added. IA-methyl red (1 mg) was dissolved in DMSO (30 µl) and an aliquot (6.6 µl) was added to the mixture, which was then incubated for 90 minutes at room temperature. The mixture was centrifuged at 10,000 rpm for 2 minutes to remove the excess IA-methyl red and the supernatant was then transferred to a fresh microcentrifuge tube. The resultant HICS probe was recovered as described in (iii).

4. Hybridisation of HICS Probe with Target Oligonucleotide

Reaction mixtures (100 µl total volume) were prepared containing the followings: lithium hydroxide (125 mM), succinic acid (95 mM), EGTA (pH 5.2, 1.5 mM), EDTA (1.5 mM), lithium lauryl sulfate (8.5%, w/v); HICS probe (100 fmol), and either 0.5 pmol of the target nucleic acid (i.e. nucleic acid complementary to the middle 28 bases of the HICS probe whose sequence is given in SEQ ID No 1, i.e. excluding the 6 bases at each end,) or 0.5 pmol of a non-complementary nucleic acid. The reaction mixtures were incubated at 60° C. for 30 min in a heating block. The product solutions were removed from the heating block and allowed to cool to room temperature. The chemiluminescence was measured using a luminometer. This involved the automatic injection of hydrogen peroxide solution (200 µl, 1.0%, v/v in 2-amino-2-(hydroxymethy)propane-1,3-diol hydrochloride (Tris-HCl) buffer solution (0.2 M, pH 9.0)), followed by measurement of signal for 10 seconds. The results are shown in FIG. 1.

5. Dose-Response of Hybridisation of HICS Probe with Target Nucleic Acid

Figure 2:
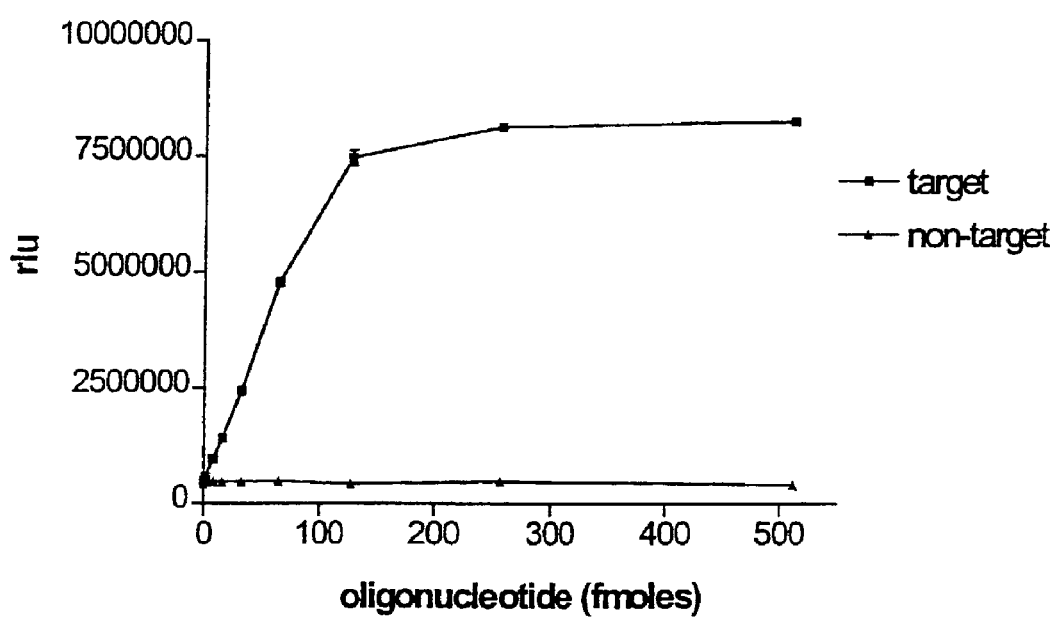
FIG. 2 is a dose/response curve obtained using a chemiluminescence/quencher-labelled oligonucleotide probe (Hybridisation Induced Chemiluminescent Signal, HICS) probe according to the invention, when bound to various amounts of target sequence and when not so bound.

Reaction mixtures (100 µl total volume) were prepared containing the following: lithium hydroxide (125 mM), succinic acid (95 mM), EGTA (pH 5.2, 1.5 mM), EDTA (1.5 mM), lithium lauryl sulfate (8.5%, w/v); HICS probe (100 fmol), and either the target nucleic acid of Example 4 (i.e. complementary to the middle 28 bases of SEQ ID No 1) at various concentrations (0–512 fmol)) or a non-complementary nucleic acid at various concentrations (0–512 fmol). The reaction mixtures were incubated at 60° C. for 30 min in a heating block. The product solutions were removed from the heating block and allowed to cool to room temperature. The chemiluminescence was measured using a luminometer. This involved the automatic injection of hydrogen peroxide solution (200 µl, 1.0%, v/v in 2-amino-2-(hydroxymethy)propane-1,3-diol hydrochloride (Tris-HCl) buffer solution (0.2 M, pH 9.0)), followed by measurement of signal for 10 seconds. The results are shown in FIG. 2.

6. Measurement of T7 Polymerase Product

A HICS probe was synthesised as above which possessed the sequence:—CCG GTC GGC CTC TTC GCT ATT ACG CCA GCT GAC CGG. (SEQ ID No.2)

A sequence complementary to the middle 24 bases of the HICS probe was also synthesised as a positive control for the following experiment. Complementary binding of the HICS probe to the above sequence is shown in FIG. 3.

T7 Polymerase in vitro transcription was performed in duplicate, including suitable controls, using a commercially available kit, Promega Corporation, according to the Manufacturer's instructions such that the enzyme product included the above target sequence. Reaction mixtures (100µl total volume) were prepared in 12×75 mm polystyrene test tubes containing the following: 125 mM lithium hydroxide, 95 mM succinic acid, pH 5.2, 0.5 mM EGTA, 1.5 mM EDTA, 8.5% (w/v) lithium lauryl sulphate; 100 fmol HICS probe and 25 µl of the T7 polymerase in vitro transcription product, diluted 1/100, 1/200, 1/400 with water. The reactions were incubated at 60° C. for 30 min in a heating block. The reactions were removed from the heating block and allowed to cool to room temperature. The chemiluminescence was measured in a luminometer by the automatic injection of 200 µl of 0.2M Tris-HCl (pH 9.0), 0.15M hydrogen peroxide, followed by measurement of the signal for 10 sec. The results are shown in FIG. 4.

7. Analysis of Mismatched Base Pairs

Reaction mixtures (100 µl total volume) were prepared in 12×75 mm polystyrene test tubes containing the following: 125 mM lithium hydroxide, 95 mM succinic acid, pH 5.2, 1.5 mM EGTA, 1.5 mM EDTA, 8.5% (w/v) lithium lauryl sulphate; 100 fmol HICS probe (sequence: CCG GTC ACG CTG TTG GGA GTC ACG GGT GAC CGG (SEQ ID No 3)) and 0–2240 fmoles of target nucleic acid (i.e. nucleic acid which is 100% complementary to the HICS probe) or 0–2240 fmoles of target nucleic acid designed with a number of altered bases (compared to the 100% complementary target) as detailed in the table below.

| Number of mismatches | Target sequence | |
|---|---|---|
| 0 | ACCCGTGACTCCCAACAGCGT | (SEQ ID No 4) |
| 1 | ACCCGTGACTCCAAACAGCGT | (SEQ ID No 5) |
| 2 | ACCCGTGACTCAAAACAGCGT | (SEQ ID No 6) |
| 4 | ACAAGTGACTCAAAACAGCGT | (SEQ ID No 7) |
| 6 | ACAAGTGACTCAAAACAAAGT | (SEQ ID No 8) |

The reactions were incubated at 60° C. for 30 min in a heating block. The reactions were removed from the heating block and allowed to cool to room temperature. The chemiluminescence was measured in a luminometer by the automatic injection of 200 µl of 0.2M Tris-HCl (pH 9.0), 0.15M hydrogen peroxide, followed by measurement of the signal for 10 sec. The results are shown in FIG. 5.

The invention claimed is:

1. A method for detecting and/or quantifying a target nucleic acid sequence in a sample comprising:

contacting said sample with an oligonucleotide sequence containing at least a probe sequence capable of binding to said target nucleic acid sequence, wherein said oligonucleotide sequence is labelled with each of at least one chemiluminescent molecule and at least one quencher molecule capable of attenuating chemiluminescence from said chemiluminescent molecule, the chemiluminescent and quencher molecules being arranged so that the interaction thereof changes according to whether the probe sequence is bound to said target nucleic acid sequence, such that in one of the bound and unbound states said chemiluminescence is substantially attenuated, and in the other thereof there is reduced or no attenuation of the chemiluminescence;

chemically activating the chemiluminescent molecule; and detecting the chemiluminescence emission from said chemiluminescent molecule and comparing said chemiluminescence emission with that corresponding to the absence of said target nucleic acid sequence thereby detecting and/or quantifying said target nucleic acid sequence.

2. A method according to claim 1, wherein, in the unbound state of the oligonucleotide sequence, the quencher molecule substantially quenches the chemiluminescence emission from said chemiluminescent molecule.

3. A method according to claim 1 or claim 2, wherein:

(i) in the absence of the target nucleic acid sequence to be detected, the chemiluminescent and quencher molecules are held in sufficiently close proximity to each other, such that chemiluminescence quenching occurs, by a bridging molecule capable of binding to the opposite end regions of said probe sequence when said end regions are positioned adjacent or substantially adjacent to each other; and (ii) in the presence of the target nucleic acid sequence to be detected, the chemiluminescent and quencher molecules are separated upon preferential binding of the probe sequence to the target nucleic acid sequence such that little or no chemiluminescence quenching occurs.

4. A method according to claim 3, wherein said bridging molecule comprises a second oligonucleotide sequence which is complementary to groups of sequential nucleotides adjacent to the two ends of the probe sequence.

5. A method according to claim 1 or claim 2, wherein:

(i) in the absence of the target nucleic acid sequence to be detected, the chemiluminescent and quencher molecules are held in sufficiently close proximity to each other due to their affinity for each other, such that chemiluminescence quenching occurs; and (ii) in the presence of the target nucleic acid sequence to be detected, the chemiluminescent and quencher molecules are separated upon preferential binding of the probe sequence to the target nucleic acid sequence such that little or no chemiluminescence quenching occurs.

6. A method according to claim 5, wherein:

(i) in the absence of the target nucleic acid sequence to be detected, the chemiluminescent and quencher molecules are held in sufficiently close proximity to each other, such that chemiluminescence quenching occurs, by the presence of flanking oligonucleotide sequences which are complementary to each other adjacent to the two ends of the probe sequence such that intra-molecular binding occurs; and (ii) in the presence of the target nucleic acid sequence to be detected, the chemiluminescent and quencher molecules are separated upon preferential binding of the probe sequence to the target nucleic acid sequence such that little or no chemiluminescence quenching occurs.

7. A method according to claim 5, wherein:

(i) in the absence of the target nucleic acid sequence to be detected, the chemiluminescent and quencher molecules are held in sufficiently close proximity to each other, such that chemiluminescence quenching occurs, by the presence of pairs of chemical species having affinity for each other and which are positioned in or comprise any of the regions of the oligonucleotide sequence comprising the following groups: probe sequence, flanking sequence, linker groups, chemiluminescent emitter, chemiluminescent quencher; and (ii) in the presence of the target nucleic acid sequence to be detected the chemiluminescent and quencher molecules are separated upon preferential binding of the probe sequence to the target nucleic acid sequence such that little or no chemiluminescence quenching occurs.

8. A method for detecting and/or quantifying a target nucleic acid sequence in a sample comprising:

contacting said sample with at least two oligonucleotides having different sequences capable of simultaneously binding to said target nucleic acid sequence, wherein said at least two oligonucleotides are labelled respectively with at least one chemiluminescent molecule and at least one quencher molecule capable of attenuating chemiluminescence when said two labelled oligonucleotides bind to said target nucleic acid sequence substantially adjacent to each other;

chemically activating the chemiluminescent molecule; and detecting the chemiluminescence emission from said chemiluminescent molecule and comparing said chemiluminescence emission with that corresponding to the absence of said target nucleic acid sequence thereby detecting and/or quantifying said target nucleic acid sequence.

9. A method for detecting and/or quantifying a target nucleic acid sequence in a sample comprising:

contacting said sample with at least two oligonucleotides capable of binding to each other, wherein said at least two oligonucleotides are labelled respectively with at least one chemiluminescent molecule and at least one quencher molecule capable of attenuating chemiluminescence when said labelled oligonucleotides are bound to each other, and wherein there is little or no attenuation of said chemiluminescence from the chemiluminescent molecule when the binding of said labelled oligonucleotides to each other is inhibited by the presence of said target nucleic acid sequence;

chemically activating the chemiluminescent molecule; and detecting the chemiluminescence emission from said chemiluminescent molecule and comparing said chemiluminescence emission obtained in the presence and absence of said target nucleic acid sequence thereby detecting and/or quantifying said target nucleic acid sequence.

10. A method according to claim 1 or claim 2, wherein at least two different target nucleic acid sequences are detected and/or quantified by use of at least two mutually distinguishable oligonucleotide systems having different sequences, each being labelled with a different chemiluminescent molecule and the same or a different quencher molecule.

11. A method according to claim 8 or 9, wherein at least two different target nucleic acid sequences are detected and/or quantified by use of at least two mutually distinguishable oligonucleotide systems, each having a different sequence capable of hybridising to a respective one of said target nucleic acid sequences and each labelled with a different chemiluminescent molecule, and at least one oligonucleotide having a different sequence capable of hybridising to at least one of said target nucleic acid sequences and labelled with a quencher molecule.

12. A method according to claim 11, wherein at least two different target nucleic acid sequences are detected and/or quantified by use of at least two oligonucleotides having different sequences each labelled with different chemiluminescent molecules and at least two oligonucleotides having different sequences and labelled with different quencher molecules.

13. A method according to claim 1 or claim 2, wherein the chemiluminescent molecules are selected from the group of compounds of which the following form a structural basis: acridine, phenanthridine, benzacridine, quinoline, and pyridine.

14. A method according to claim 13, wherein the chemiluminescent molecule is an acridinium salt.

15. A method according claim 13, wherein the chemiluminescent molecule is an acridan.

16. A method according to claim 1 or claim 2, wherein the chemiluminescent molecule emits light within the wavelength range 200–700 nm.

17. A method according to claim 1 or claim 2, wherein the quencher molecule absorbs light within the wavelength range 200–700 nm.

18. A method according to claim 1 or claim 2, wherein the quencher molecule is an azo dye.

19. A method according to claim 1 or claim 2, wherein the quencher molecule is a derivative of methyl red.

20. A labelled oligonucleotide for detecting and/or quantifying a target nucleic acid sequence comprising an oligonucleotide probe sequence capable of binding to said target nucleic acid sequence, said oligonucleotide being labelled with a chemiluminescent molecule requiring chemical activation and a quencher molecule and being arranged such that the quencher molecule and the chemiluminescent molecule requiring chemical activation interact to cause a change in a subsequent chemiluminescent emission according to whether the labelled oligonucleotide is bound to said target nucleic acid sequence.

21. A labelled oligonucleotide according to claim 20, wherein, when not bound to said target nucleic acid sequence, said quencher molecule causes quenching of said chemiluminescence, but binding to said target nucleic acid sequence prevents or reduces said quenching.

22. A labelled oligonucleotide according to claim 20 or claim 21, wherein said oligonucleotide is between 15 and 45 nucleotide.

23. A labelled oligonucleotide according to claim 20 or claim 21, wherein said chemiluminescent molecule is an acridinium salt.

24. A labelled oligonucleotide according to claim 20 or claim 21, wherein said quencher molecule is an azo dye.

25. A labelled oligonucleotide according to claim 24, wherein said quencher molecule is a derivative of methyl red.

26. A kit comprising a labelled oligonucleotide according to claim 20 or claim 21 and reagent means for initiating said chemiluminescent reaction.

* * * * *